(12) United States Patent
Dees, Jr.

(10) Patent No.: US 11,638,776 B1
(45) Date of Patent: May 2, 2023

(54) MEDICAL DEVICES AND METHODS FOR FORMING MEDICAL DEVICES HAVING A POROUS STRUCTURE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventor: Roger Ryan Dees, Jr., Drummonds, TN (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 265 days.

(21) Appl. No.: 17/063,504

(22) Filed: Oct. 5, 2020

Related U.S. Application Data

(60) Provisional application No. 62/911,690, filed on Oct. 7, 2019.

(51) Int. Cl.
*A61L 24/00* (2006.01)
*A61L 27/56* (2006.01)
*A61L 27/06* (2006.01)
*A61L 27/04* (2006.01)
*A61L 27/30* (2006.01)
*B33Y 80/00* (2015.01)

(52) U.S. Cl.
CPC ............. *A61L 27/06* (2013.01); *A61L 27/045* (2013.01); *A61L 27/306* (2013.01); *A61L 27/56* (2013.01); *B33Y 80/00* (2014.12); *A61L 2420/02* (2013.01); *A61L 2430/02* (2013.01)

(58) Field of Classification Search
CPC ... A61L 2420/02; A61L 2400/18; C23C 4/02; C23C 4/04; C23C 4/06; C23C 4/134
See application file for complete search history.

(56) References Cited

U.S. PATENT DOCUMENTS

| 4,542,539 A | * | 9/1985 | Rowe, Jr. .................. A61F 2/30 606/76 |
| 4,550,448 A | * | 11/1985 | Kenna ................. A61F 2/30767 606/76 |
| 4,865,608 A | * | 9/1989 | Brooker, Jr. ........ A61F 2/30767 623/23.29 |

(Continued)

OTHER PUBLICATIONS

Jemat. et al. Surface Modifications and Their Effects on Titanium Dental Implants.Surface Modifications and Their Effects on Titanium Dental Implants. vol. 2015, Article ID 791725, 11 pages, 2015. https://doi.org/10.1155/2015/791725 (Year: 2015).*

*Primary Examiner* — Cachet I Proctor
(74) *Attorney, Agent, or Firm* — KDW Firm PLLC

(57) ABSTRACT

Medical devices, such as orthopedic medical implants, and corresponding methods of applying a porous coating to the medical device are disclosed. In some embodiments, a medical device may include a plurality of texture features extending from a base surface, and a porous coating applied into and atop of the plurality of texture features and the base surface. The porous coating may include a plurality of coating structures, wherein a first coating structure group of the plurality of coating structures has a first size, wherein a second coating structure group of the plurality of coating structures has a second size, and wherein the first size is different than the second size.

15 Claims, 4 Drawing Sheets

(56) References Cited

U.S. PATENT DOCUMENTS

| | | | | |
|---|---|---|---|---|
| 6,350,126 | B1* | 2/2002 | Levisman | A61C 8/0033 433/1 |
| 7,144,428 | B2* | 12/2006 | Anitua | A61L 27/06 623/923 |
| 8,066,763 | B2* | 11/2011 | Alt | A61F 2/91 623/1.45 |
| 8,066,770 | B2* | 11/2011 | Rivard | A61F 2/30767 623/23.55 |
| 8,449,603 | B2* | 5/2013 | Weber | A61L 31/146 623/1.48 |
| 8,475,536 | B2* | 7/2013 | Tong | A61F 2/30767 623/23.57 |
| 8,696,759 | B2* | 4/2014 | Tong | A61L 27/50 427/2.26 |
| 9,023,419 | B2* | 5/2015 | Meehan | C23C 4/06 427/446 |
| 10,426,577 | B2* | 10/2019 | Mandanici | C23F 1/30 |
| 2006/0289388 | A1* | 12/2006 | Yang | A61L 27/50 216/96 |
| 2010/0057197 | A1* | 3/2010 | Weber | A61L 27/30 607/116 |
| 2011/0014258 | A1* | 1/2011 | Gan | A61L 27/30 514/420 |
| 2012/0041412 | A1* | 2/2012 | Roth | A61M 37/0015 604/103.02 |
| 2015/0272750 | A1* | 10/2015 | Roth | A61F 2/92 623/1.15 |
| 2017/0173225 | A1* | 6/2017 | Troxel | A61L 31/10 |
| 2019/0091027 | A1* | 3/2019 | Asaad | A61F 2/447 |
| 2019/0192303 | A1* | 6/2019 | Gallagher | A61P 19/08 |
| 2019/0298533 | A1 | 10/2019 | Kane | |
| 2021/0319984 | A1* | 10/2021 | Weichart | H01J 37/321 |

\* cited by examiner

MEDICAL DEVICES AND METHODS FOR FORMING MEDICAL DEVICES HAVING A POROUS STRUCTURE

CROSS-REFERENCE TO RELATED APPLICATIONS

This is a non-provisional of, and claims the benefit of the filing date of, U.S. provisional patent application No. 62/911,690, filed Oct. 7, 2019, entitled "Medical Devices and Methods for Forming Medical Devices Having a Porous Structure," the entirety of which application is incorporated by reference herein.

TECHNICAL FIELD

The present disclosure generally relates to medical devices, and more particularly, but not exclusively, to medical devices, such as implants, and methods of coating a surface of the implants to produce an enhanced porous coating morphology.

BACKGROUND

Certain medical devices, such as orthopedic implants, have a surface coating designed to enhance osseointegration. Orthopedic implants include, but are not limited to, bone plates, intermedullary nails, hip implants, knee implants, shoulder implants, spinal implants, etc. Surface coatings may be textured or porous to more closely resemble trabecular bone. Porous surface coatings have interconnecting networks of pores, which are similar to those of trabecular bone, and may serve to promote bone ingrowth into the porous coating and provide better long-term implant fixation. Adhesion between the implant and bone depends, in part, on the thickness and porosity of the coating. For example, powder size of the coating may be varied to manipulate pore size and/or porosity. However, when the powder size is increased, attachment strength between the porous coating and the implant typically decreases. Decreasing powder size aids with adhesion, but decreases the porosity of the coating. Therefore, a compromise takes place, and porosity typically stays at the lower end to maintain attachment strength.

A similar compromise can be seen for coating thickness. As layers of coating are added to increase thickness, attachment strength between the porous coating and the implant typically declines. With larger powder size, whether symmetric or asymmetric, attachment points are reduced per volume, resulting in reduced attachment strength.

Spray coating metallic implants can be particularly problematic. For example, porous plasma spraying titanium onto a metallic surface produce reduced porosity percentages and/or attachment strength.

For a number of reasons, it would be beneficial to utilize methods for coating medical devices, such as implants, with a porous coating that produces enhanced coating morphology (e.g., increased pore sizes and/or porosity). In particular, it would be beneficial to improve methods for spray coating metallic implants with a porous plasma sprayed titanium coating. As such, a need remains for further improvements in this technological field. The present disclosure addresses this need.

SUMMARY

The Summary is provided to introduce a selection of concepts in a simplified form, the concepts further described below in the Detailed Description. The Summary is not intended to identify key features or essential features of the claimed subject matter, nor is the Summary intended as an aid in determining the scope of the claimed subject matter.

Approaches for forming medical devices, such as implants, having a porous coating, are disclosed. In one embodiment, a medical device may include a plurality of texture features extending from a base surface and a porous coating formed over the plurality of texture features and the base surface. The porous coating may include a plurality of coating structures, wherein a first coating structure group of the plurality of coating structures has a first size, wherein one or more coating structures of the first coating structure group is in direct contact with the plurality of texture features or the base surface, wherein a second coating structure group of the plurality of coating structures has a second size, and wherein the first size is less than the second size.

In another embodiment, a method of forming a medical implant may include patterning a plurality of texture features from a substrate, and forming a porous coating over the substrate. The porous coating may include a plurality of coating structures, wherein a first coating structure group of the plurality of coating structures has a first size, wherein one or more coating structures of the first coating structure group is in direct contact with the plurality of texture features or the base surface, wherein a second coating structure group of the plurality of coating structures has a second size, and wherein the first size is less than the second size.

In yet another embodiment, an implant may include a plurality of texture features extending from a base surface, and a porous coating formed over the plurality of texture features and the base surface. The porous coating may include a plurality of coating structures, wherein a first coating structure group of the plurality of coating structures has a first size, a first porosity, and a first pore size, wherein a second coating structure group of the plurality of coating structures has a second size, a second porosity, and a second pore size, wherein the first size is less than the second size, wherein the first porosity is less than the second porosity or the first pore size is less than the second pore size, and wherein one or more coating structures of the first coating structure group is in direct contact with the plurality of texture features or the base surface.

In these and other embodiments, the implant surface is treated prior to receiving the porous coating in order to enhance porous coating morphology. The implant surface preparation can be achieved through texturization via, for example, chemical etching, mechanical etching/grooving, laser etching, or other texturing mechanisms. The texture can be symmetric or asymmetric, 2-D or 3-D. Increased spacing and depth of the etched implant surface allows a reduction in coating layers, while still achieving a desired pore morphology. In one embodiment, the porous coating is a porous plasma sprayed titanium coating applied to a metallic implant. In one embodiment, the thickness of the porous plasma sprayed titanium coating is approximately equal to the height of the texturization (e.g., textured surface), or slightly larger than the height of the textured surface.

Embodiments of the present disclosure provide numerous advantages. For example, the embodiments provide, inter alia, enhance porous coating morphology (e.g., increased pore size and/or porosity), and improved adhesion of the porous coating to the implant. In addition, in one embodiment, the embodiments facilitate porous plasma sprayed titanium to be applied to metallic implants with enhanced pore morphology and increased adhesion strength.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

The accompanying drawings illustrate exemplary approaches of the disclosure, including the practical application of the principles thereof, as follows.

Figure 1:
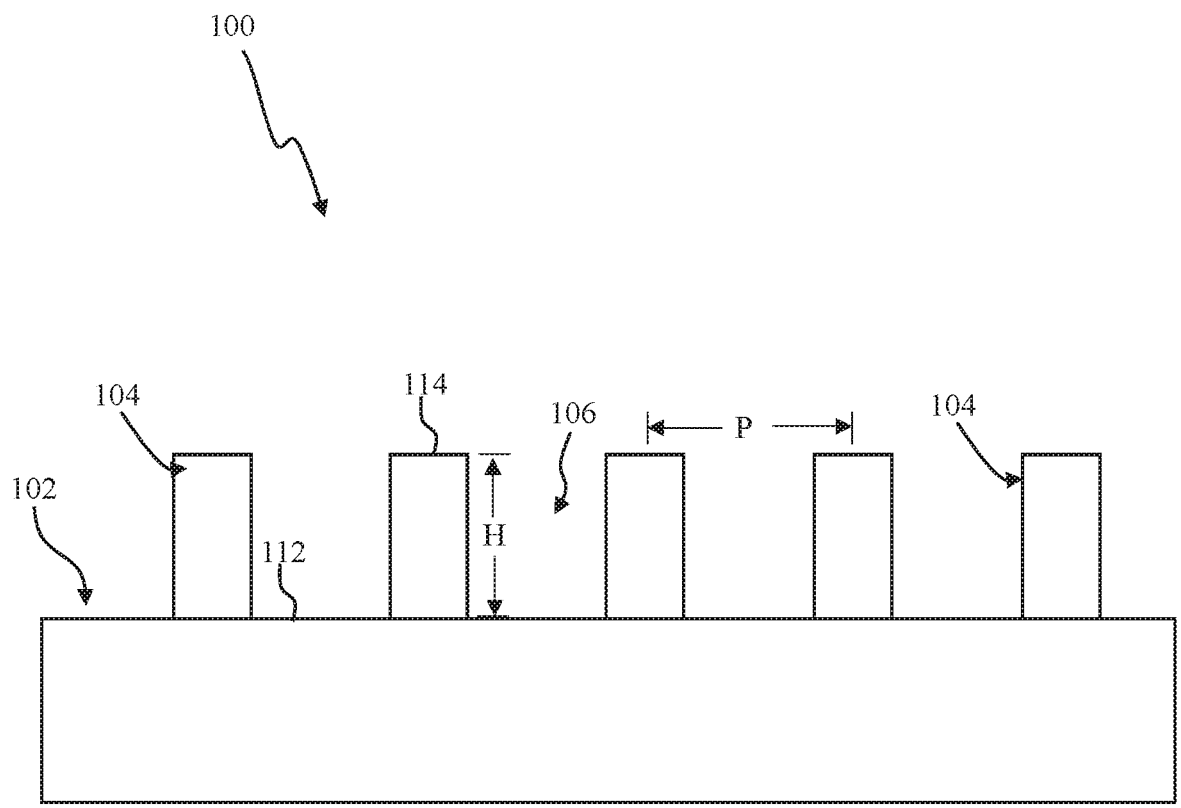
FIG. 1 illustrates a side, cross-sectional view of a surface of a medical implant, in accordance with one feature of the present disclosure.

The drawings are not necessarily to scale. The drawings are merely representations, not intended to portray specific parameters of the disclosure. The drawings are intended to depict example embodiments of the disclosure, and therefore are not to be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DESCRIPTION

For the purposes of promoting an understanding of the principles of the present disclosure, reference will now be made to example embodiments. It will nevertheless be understood that no limitation of the scope of the disclosure is thereby intended. Any alterations and further modifications in the described embodiments, and any further applications of the principles of the present disclosure as described herein are contemplated as would normally occur to one skilled in the art to which the disclosure relates.

The present disclosure is directed to systems and methods of coating a medical device with a porous coating surface. In one embodiment, one or more surfaces of the medical device is textured, etched, and/or otherwise prepared prior to coating in order to enhance the resulting porous coating morphology. More specifically, the surface of the medical device is initially treated in a manner arranged and configured to produce increased pore size and/or pore spacing in the subsequently applied porous coating. In addition, the treatment may be arranged and configured to produce increased tensile attachment strength between the porous coating and the implant.

Referring to FIG. 1, a surface 102 of a medical device 100 or a medical implant according to one example embodiment will be described. As shown, medical device (hereinafter "device") 100 may be a solid structure having a plurality of texture features 104 separated by a plurality of grooves, valleys, or indentations 106 formed therein. As used herein, the device 100 may be any suitable implant or medical device now known or hereafter developed. For example, in some embodiments, the device 100 may be a bone plate, a hip implant, a knee implant, etc. Embodiments of the present disclosure are not limited in this context.

The device 100 may be formed by any variety of processes. Furthermore, the device 100 may be made from any suitable material such as, for example, titanium, commercially pure titanium, titanium alloy, cobalt-chromium, stainless steel, zirconium, oxidized zirconium, etc. The texture features 104 and the indentations 106 may be formed in the surface 102 of the device 100 via any suitable mechanism now known or hereafter developed such as, for example, mechanical etching/grooving (e.g., machining, shaping, scribing, knurling, etc.), laser etching/texturing, chemical etching, or other texturing mechanisms. In some embodiments, the texture etching can be symmetric and/or asymmetric, 2-D or 3-D, with a purpose of attaining improved porosity (e.g., pore size/spacing) and a desired thickness for a subsequent porous coating application.

In various embodiments, the texture features 104 and the indentations 106 may be formed by sharp grooves, curved grooves, undercut features, etc. Although the texture features 104 are shown as being generally rectangular-shaped, it will be appreciated that the texture features 104 and the indentations 106 may take on different shapes in other embodiments The textured coating surface provides more surface area and, in some areas, more than one point of contact between the substrate and a same coating structure of a porous coating. As a result, the number of coating structures in direct contact with the substrate versus those coating structures in direct contact with only other coating structures, may be increased, thus providing greater adhesion between the porous coating and the surface of the substrate. It will be appreciated that greater or lesser points of contact may exist depending on the type/shape of porous coating and/or the type/shape of the texture features 104 and the indentations 106.

As shown, the texture features 104 may define a vertical height 'H' measured from a base surface 112 of the indentations 106 to a top 114 of the texture features 104. Furthermore, the texture features 104 may define a pitch 'P' between adjacent texture features 104. In some embodiments, the height and/or pitch are substantially uniform across the device 100 for each of the texture features 104 and indentations 106. In other embodiments, the height and/or pitch of the texture features 104 can vary. Embodiments herein are not limited in this context.

Figure 2:
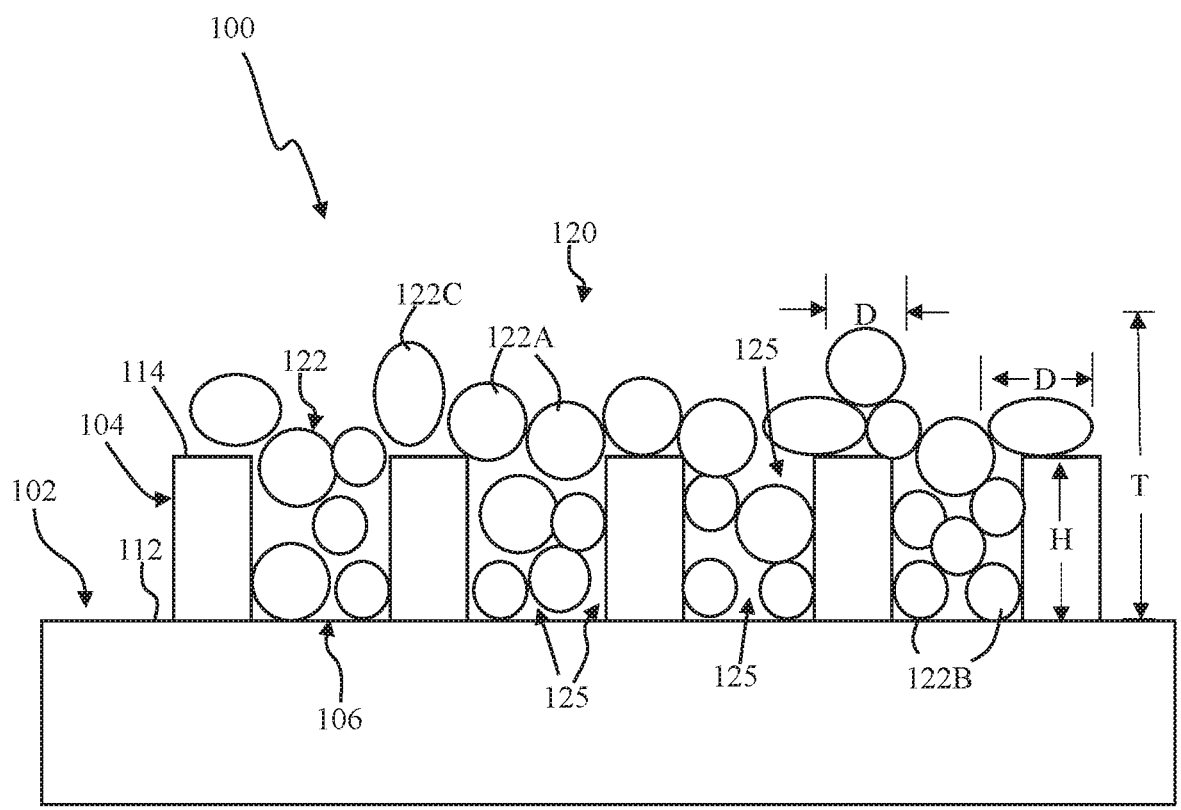
FIG. 2 illustrates a side, cross-sectional view of the surface of the medical implant of FIG. 1 with a porous coating formed thereon, in accordance with one feature of the present disclosure.

In FIG. 2, a porous coating 120 may be formed over, built on, applied, sprayed, or the like, to the device 100. As shown, the porous coating 120 may include a plurality of coating structures (e.g., beads) 122 disposed within the indentations 106 and over the texture features 104. Although non-limiting, the coating structures 122 may be spherically shaped and made from one or more polymers, one or more metals, sand, or other material(s). For example, the coating structures 122 may be cobalt chrome, titanium, zirconium, stainless steel, or other implantable materials (e.g. ceramic, PEEK) in a form of symmetric or asymmetric beads and/or particles, plasma sprayed, vapor deposition, and/or other means of application-specific forms. The coating structures 122 may each have a width dimension, such as a diameter 'D'. In some embodiments, the plurality of coating structures 122 may include first and second groups of coating structures. In one embodiment, the first and second groups may have different widths or diameters. For example, the plurality of coating structures 122 may include a larger diameter group of coating structures and a smaller diameter group of coating structures. That is, as illustrated, in one embodiment, a larger diameter group 122A of the plurality of coating structures 122 has a first size (e.g., diameter), and a smaller diameter group 122B of the plurality of coating structures 122 has a second size (e.g., diameter), wherein the first size is different (i.e., greater) than the second size. Furthermore, in some embodiments, one or more of the plurality of coating structures 122 may have a different shape. For example, coating structure 122C may generally have an oval shape. Embodiments herein are not limited in this context, however.

Although non-limiting, the porous coating 120 has a thickness 'T', relative to a plane defined by the base surface 112. In some embodiments, the thickness of the porous coating 120 is greater, lesser than, or equal to the height of the texture features 104. Although not shown, the porous coating 120 may have a generally planer upper surface after application. In some embodiments, the thickness T of the porous coating 120 is approximately equal to the height H of the textured surface, or slightly larger than the height H of the textured surface. In one embodiment, a coating mean thickness measured from the base surface 112 may be between 500-1500 micrometers. The texturized surface may have a height of between 200-1500 micrometers. In one embodiment, the textured surface may have a height between 500-1500 micrometers. In one embodiment, the thickness T of the porous coating may be larger (e.g., taller) than the height H of the texturized surface so that the texturized surface is shorter than the height of the porous coating with the porous coating extending above the texturized surface. For example, in one embodiment, the thickness T of the porous coating may be approximately 500 urn min, while the height H of the texturized surface may be approximately 200-300 urn min. Alternatively, in one embodiment, the thickness T of the porous coating is approximately 1000 micrometers, while the height H of the texturized surface is approximately 500 micrometers. However, the thickness/height of the porous coating 120 and the textured surface may vary as desired, e.g., based on pore morphology, attachment strength, coating type/shape, texturing type/shape, etc. Embodiments herein are not limited in this context.

As shown, spaces between each of the plurality of coating structures 122 represent pores 125 of the porous coating 120. By varying the dimensions and shapes of the plurality of coating structures 122, pore size can be modified. In some embodiments, it may be desirable to increase or decrease the size of the pores 125, either uniformly across the thickness of the porous coating 120, or just in targeted areas of the porous coating 120. For example, smaller diameter coating structures 122B may be first applied atop the base surface 112 between the indentations 106, followed by the relatively larger diameter coating structures 122A. As a result, the size of the pores 125 closer to the base surface 112 may be smaller than those pores 125 closer to the top 114 of the texture features 104. Thus arranged, the smaller diameter coating structures 122B initially provide increased tensile attachment strength. Thereafter, the subsequently applied, larger diameter coating structures 122A facilitate creation of enhanced pore morphology (e.g., increased porosity and/or pore size). In other embodiments, a substantially equal amount of larger and smaller diameter coating structures 122A, 122B may be deposited atop the device 100 to provide a more uniform porosity throughout the porous coating 120. In one embodiment, the smaller diameter coating structures 122B may have a size between 10-20 μm. The larger diameter coating structures 122A may have a size between 40-350 μm.

Figure 3:
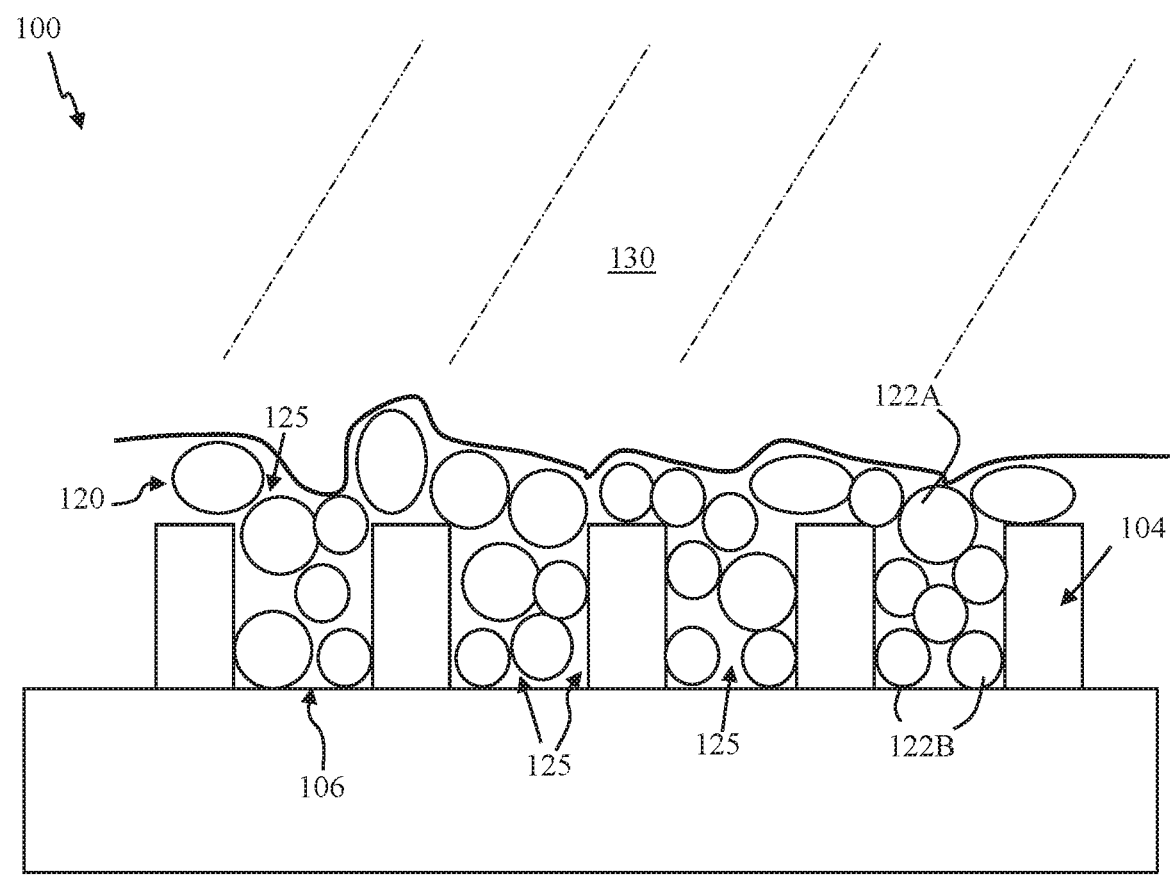
FIG. 3 illustrates a side, cross-sectional view of the porous coating of FIG. 2 engaged with a bone, in accordance with one feature of the present disclosure.

As shown in FIG. 3, in use, the porous coating 120 may contact a patient's bone 130. In one example embodiment, the porous coating 120 is formed by plasma-sprayed metal, such as titanium. As will be appreciated, plasma-sprayed titanium tends to be extremely dense resulting in coatings having reduced porosity and/or pore sizes, and reduced tensile attachment strength. In accordance with the principles of the present disclosure, by initially texturizing the surface of the device, plasma-sprayed titanium may be applied to the surface of the device. In one embodiment, the height H of the texturization is approximately equal to the height of the desired coating. By initially texturizing the surface of the implant, manufacturers are able to spray less material with varying grain size (e.g., initially spraying smaller bead sizes to provide initial tensile attachment strength) and subsequently increasing the bead size to provide increased pore morphology. In use, the texturized features act to move the plasma-sprayed titanium away from the surface of the device. Plasma sprayed coatings may form a three-dimensional interconnected array of pores 125. Tissue of the live bone 130 will integrate into a portion of the pores 125, providing enhanced implant fixation.

Figure 4:
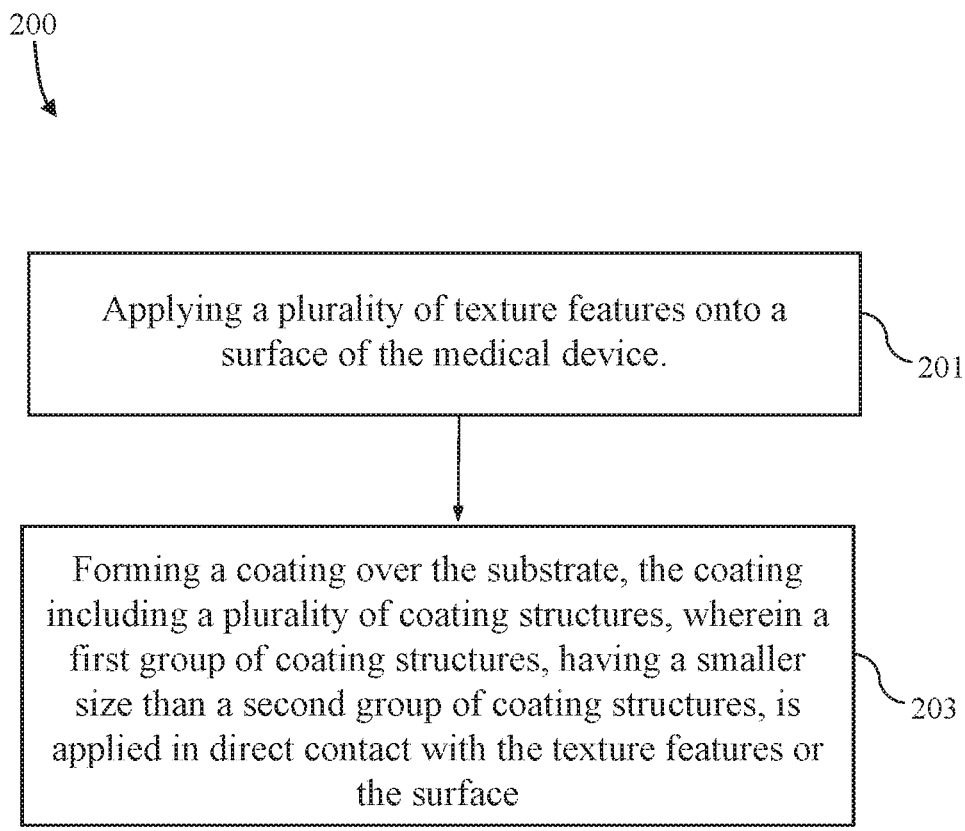
FIG. 4 a flowchart illustrating a method for forming a medical device in accordance with one feature of the present disclosure.

Referring now to FIG. 4, an example of a method 200 for forming a medical device, such as an implant, will be described in greater detail. At block 201, the method 200 includes applying a plurality of texture features onto a surface of the medical device. In some embodiments, the plurality of texture features may be applied in a uniform or non-uniform manner. For example, the plurality of texture features may be applied in a uniform height and/or pitch. In some embodiments, the texture features and the indentations may be formed in a surface of the device via mechanical etching/grooving (e.g., machining, shaping, scribing, knurling, etc.), laser etching/texturing, chemical etching, or other texturing means. In some embodiments, the texture etching can be symmetric and/or asymmetric, 2-D or 3-D.

At block 203, the method 200 may include forming a coating over the substrate, the coating comprising a plurality of coating structures, wherein a first coating structure group of the plurality of coating structures has a first size, wherein one or more coating structures of the first coating structure group is in direct contact with the plurality of texture features or the base surface, wherein a second coating structure group of the plurality of coating structures has a second size, and wherein the first size is less than the second size. In some embodiments, the first coating structure group of the plurality of coating structures has a first porosity and a first pore size, and the second coating structure group has a second porosity and a second pore size, wherein the first porosity is less than the second porosity or the first pore size is less than the second pore size.

In some embodiments, the porous coating is formed by plasma spraying titanium over the substrate, including over the plurality of texture features. In some embodiments, forming the porous coating includes plasma spraying cobalt chrome, titanium, zirconium, oxidized zirconium, or stainless steel over the substrate, including over the plurality of texture features. In one embodiment, the coating may have a height substantially equal to the height of the texturized surface.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other.

Furthermore, identification references (e.g., primary, secondary, first, second, third, fourth, etc.) are not intended to connote importance or priority, but are used to distinguish one feature from another. The drawings are for purposes of illustration only and the dimensions, positions, order and relative sizes reflected in the drawings attached hereto may vary.

Furthermore, the terms "substantial" or "substantially," as well as the terms "approximate" or "approximately," can be used interchangeably in some embodiments, and can be described using any relative measures acceptable by one of ordinary skill in the art. For example, these terms can serve as a comparison to a reference parameter, to indicate a deviation capable of providing the intended function. Although non-limiting, the deviation from the reference parameter can be, for example, in an amount of less than 1%, less than 3%, less than 5%, less than 10%, less than 15%, less than 20%, and so on.

Still furthermore, although the illustrative methods are described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure. Furthermore, the methods may be implemented in association with the formation and/or processing of structures illustrated and described herein as well as in association with other structures not illustrated.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, the present disclosure has been described herein in the context of a particular implementation in a particular environment for a particular purpose. Those of ordinary skill in the art will recognize the usefulness is not limited thereto and the present disclosure may be beneficially implemented in any number of environments for any number of purposes.

The invention claimed is:

1. A method of coating an orthopedic medical implant, the method comprising:
    forming a plurality of texture features in an outer surface of the implant, adjacent texture features separated by an indentation; and
    forming a porous coating atop the outer surface within the indentations between the plurality of texture features and over the plurality of texture features;
    wherein the porous coating includes a plurality of coating structures including a first coating structure group having a first size and a second coating structure group having a second size, the first size is less than the second size, wherein the plurality of texture features have a height and the porous coating has a thickness, and wherein the thickness of the porous coating is less than or equal to the height of the plurality of texture features.

2. The method of claim 1, wherein one or more of the coating structures of the first coating structure group is in direct contact with the plurality of texture features, the outer surface, or a combination thereof.

3. The method of claim 1, wherein forming the porous coating comprises:
    initially applying the first coating structure group atop the outer surface within the indentations between the plurality of texture features and over the plurality of texture features; and
    subsequently applying the second coating structure group.

4. The method of claim 1, wherein the plurality of texture features are applied in a uniform manner with each texture feature of the plurality of texture features has a uniform height and a uniform pitch between adjacent texture features.

5. The method of claim 1, wherein the plurality of texture features are applied in a non-uniform manner with the plurality of texture features having a non-uniform height and a non-uniform pitch between adjacent texture features.

6. The method of claim 1, wherein the plurality of texture features and indentations are formed in the outer surface using one of mechanical etching, grooving, laser etching, chemical etching, or three-dimensional printing.

7. The method of claim 1, wherein the first coating structure group has a first porosity and the second coating structure group has a second porosity, the first porosity is less than the second porosity.

8. The method of claim 1, wherein the first coating structure group has a first pore size and the second coating structure group has a second pore size, the first pore size is less than the second pore size.

9. The method of claim 1, wherein forming the porous coating includes plasma spraying titanium over the outer surface and the plurality of texture surfaces.

10. The method of claim 1, wherein the implant including the outer surface and the plurality of texture features are manufactured from one of titanium, commercially pure titanium, titanium alloy, cobalt-chromium, stainless steel, zirconium, and oxidized zirconium, and the porous coating is a titanium spray coating.

11. An orthopedic medical implant comprising
    a base surface;
    a plurality of texture features extending from the base surface, the plurality of texture features defining an indentation between adjacent texture features; and a porous coating formed over the plurality of texture features and the base surface;

wherein the porous coating includes a plurality of coating structures including a first coating structure group having a first size and a second coating structure group having a second size, and wherein the first size is less than the second size; and wherein the plurality of texture features have a height and the porous coating has a thickness, and wherein the thickness of the porous coating is less than or equal to the height of the plurality of texture features.

12. The implant of claim 11, wherein one or more coating structures of the first coating structure group is in direct contact with the plurality of texture features, the base surface, or a combination thereof.

13. The implant of claim 11, wherein the first coating structure group has a first porosity and the second coating structure group has a second porosity, the first porosity is less than the second porosity.

14. The implant of claim 11, wherein the first coating structure group has a first pore size and the second coating structure group has a second pore size, the first pore size is less than the second pore size.

15. The implant of claim 11, wherein the implant including the outer surface and the plurality of texture features are manufactured from one of titanium, commercially pure titanium, titanium alloy, cobalt-chromium, stainless steel, zirconium, and oxidized zirconium, and the porous coating is a titanium spray coating.

* * * * *